United States Patent [19]

Calhoun

[11] Patent Number: 5,468,629
[45] Date of Patent: Nov. 21, 1995

[54] METHOD OF PROMOTING IN VITRO HOMOLOGOUS RECOMBINATION TRANSFECTION IN MAMMALIAN CELLS USING THE RECA PROTEIN

[76] Inventor: Cornelia Calhoun, 3638 Washington St., San Francisco, Calif. 94115

[21] Appl. No.: 47,154

[22] Filed: Apr. 13, 1993

[51] Int. Cl.⁶ .................................................... C12N 15/90
[52] U.S. Cl. ................................... 435/172.3; 435/240.2
[58] Field of Search .............................. 435/4, 6, 172.1, 435/172.3, 240.2

[56] References Cited

U.S. PATENT DOCUMENTS

| | | | |
|---|---|---|---|
| 4,637,980 | 1/1987 | Auerbach et al. | 435/172.3 X |
| 4,818,680 | 4/1989 | Collins et al. | 435/6 |
| 4,843,006 | 6/1989 | Bittner | 435/172.3 |
| 4,888,274 | 12/1989 | Radding et al. | 435/6 |
| 4,950,599 | 8/1990 | Bertling | 435/172.3 |
| 4,963,487 | 10/1990 | Schimmel | 435/172.3 |
| 5,015,569 | 5/1991 | Pontius | 435/6 |
| 5,087,617 | 2/1992 | Smith | 514/44 |
| 5,098,890 | 3/1992 | Gewirtz et al. | 514/44 |

OTHER PUBLICATIONS

Ayala et al. (1980) Modern Genetics (Benjamin/Cummings Publishing Co., Menlo Park, Calif.) pp. 88–89.
Alonso, J. (1993) J. Biol. Chem. 268:1424–1429.
Cerutti, H. et al. (1992) Proc. Nat. Acad. Sci. 89:8068–8072.
Chen, T. R. (1988) Cytogenet. Cell Genet. 48:19–24.
Cheng, S. et al. (1988) J. Biol. Chem. 263:15110–15117.
Clark, A. and A. Margulies (1965) Proc. Nat. Acad. Sci. 53: 451–459.
Cotton, M. et al. (1992) Proc. Nat. Acad. Sci. 89:6094–6098.
Dai, Y. et al. (1992) Proc. Nat. Acad. Sci. 89:10892–10895.
Davis, A. et al. (1992) Mol. Cell. Biol. 12:2769–2776.
Dorin, J. et al. (1992) Nature 359:211–215.
Folger, L. et al. (1982) Mol. Cell. Biol. 2:1372–1387.
Golub, E. et al. (1992) Nucleic Acids Res. 20:3121–3125.
Graham, F. and A. van de Eb (1973) J. Virology 52:456–467.
Gutierrez-Ramos, J. and R. Palacios (1992) Proc. Nat. Acad. Sci. 89:9171–9175.
Huijzer, J. and M. Smerdon (1992) Biochemistry 31:5077–5084.
Hamatake, R. and M. Smerdon (1992) Biochemistry 31:5077–5084.
Kallioniemi, A. et al. (1992) Science 258:818–821.
Kemic, E. and W. Holloman (1986) Cell 44:545–554.
Kirkpatrick, D. et al. (1992) Nucleic Acids Res. 20:4339–4346.
Kolodner, R. et al. (1987) Proc. Nat. Acad. Sci. 84:5560–5564.

Koob, M. et al. (1992) Nucleic Acids Res. 20:5831–5836.
Kowalczykowski, S. (1991) Ann. Rev. Biophys. Biophysical Chem. 20:539–575.
La Salle, G. et al. (1993) Science 259:988–990.
Lawrence, J. et al. (1989) Cell 57:493–502.
Lion, T. and O. Haas. (1990) Anal. Biochem. 188:335–337.
Mannino, R. and S. Gould-Fogerite (1988) BioTechniques 6:682–690.
Moore, S. and R. Fishel (1990) Biol. Chem. 265:1108–1117.
Pinkel, D. et al. (1986) Proc. Nat. Acad. Sci. 82:2934–2938.
Radding, C. M. (1989) Biochim. Biophys. Acta 1008:131–139.
Radding, C. J. (1991) J. Biol. Chem. 266:5355–5358.
Ratajczak, M. et al. (1992) Proc. Nat. Acad. Sci. 89:11823–11827.
Sauer, B. and N. Henderson (1988) Nucleic Acids Res. 17:147–161.
Schowalter, D. and S. Sommer (1989) Ann. Biochem. 177:90–94.
Shigekawa, K. and W. Dower (1988) BioTechniques 6:742–751.
Singer, R. et al. (1986) BioTechniques 4:230–250.
Tan, W. et al. (1992) Science 258:778–781.
Thomas, K. and M. Capecchi (1987) Cell 51:503–512.
Wagner, E. et al. (1992) Proc. Nat. Acad. Sci. 89:6099–6103.

*Primary Examiner*—Richard A. Schwartz
*Assistant Examiner*—Philip W. Carter
*Attorney, Agent, or Firm*—Graham & James

[57] ABSTRACT

A rapid method for transfection of a cell under physiological conditions suitable to the survival and growth of the cell is disclosed. According to the method, a stable nucleoprotein complex is provided. The nucleoprotein complex comprises a single-stranded DNA sequence in stable combination with RecA protein molecules. Cells to be transformed are cultured in a physiologically suitable medium to which the nucleoprotein complex has been added. As the cells grow and undergo mitosis, the nucleoprotein complex is taken up within some of the cells and becomes integrated into the genome. The method accomplishes transfection without resort to infectious vectors or permeabilization or other manipulation of the cell membrane. According to another object of the invention, a diagnostics method is provided. A directly detectable reporter label or an indirectly detectable ligand is bound to the nucleoprotein complex to provide a DNA probe which then is taken up into the cell and integrates into the cell's genome. Upon appropriate treatment the detectable reporter label can be observed or the ligand can be reacted with a suitable detectable reporter molecule to allow visualization and thereby confirm whether the compliment of the DNA sequence in the probe is substantially present in the genome of the cell.

4 Claims, 7 Drawing Sheets

METHOD OF PROMOTING IN VITRO HOMOLOGOUS RECOMBINATION TRANSFECTION IN MAMMALIAN CELLS USING THE RECA PROTEIN

FIELD OF INVENTION

The present invention relates to a method for in vivo nucleic acid sequence targeting for the purpose of identifying, blocking, altering, or replacing (transplacement) specific gene sequences in mammalian cells.

References

Alonso, J. (1993) J. Biol. Chem. 268:1424–1429.

Cerutti, H. et al. (1992) Proc. Nat. Acad. Sci. 89:8068–8072.

Chen, T. (1988) Cytogenet. Cell Genet. 48:19–24.

Cheng, S. et al. (1988) J. Biol. Chem. 263:15110–15117.

Clark, A. and A. Marguiles (1965) Proc. Nat. Acad. Sci. 53:451–459.

Cotten, M. et al. (1992) Proc. Nat. Acad. Sci. 89:6094–6098.

Dai, Y. et al. (1992) Proc. Nat. Acad. Sci. 89:10892–10895.

Davis, A. et al. (1992) Mol. Cell. Biol. 12:2769–2776.

Dorin, J. et al. (1992) Nature 359:211–215.

Folger, K. et al. (1982) Mol. Cell. Biol. 2:1372–1387.

Golub, E. et al. (1992) Nucleic Acids Res. 20:3121–3125.

Graham, F. and A. van de Eb (1973) Virology 52:456–467.

Gutierrez-Ramos, J. and R. Palacios (1992) Proc. Nat. Acad. Sci. 89:9171–9175.

Hamatake, R. et al. (1989) J. Biol. Chem. 264:13336–13342.

Huijzer, J. and M. Smerdon (1992) Biochemistry 31:5077–5084.

Kallioniemi, A. et al. (1992) Science 258:818–821.

Kmiec, E. and W. Holloman (1986) Cell 44:545–554.

Kirkpatrick, D. and C. Radding (1992) Nucleic Acid Res. 20:4347–4353.

Kirkpatrick, D. et al. (1992) Nucleic Acids Res. 20:4339–4346.

Kolodner, R. et al. (1987) Proc. Nat. Acad. Sci. 84:5560–5564.

Koob, M. Pers. Comm.

Kowalczykowski, S. (1991) Ann. Rev. Biophys. Biophysical Chem. 20:539–575.

Kricka, L. (Ed.) (1992) Non-isotopic DNA Probe Techniques. Academic Press, Inc. New York, N.Y.

La Salle, G. et al. (1993) Science 259:988–990.

Lavery, P. and S. Kowalczykowski (1992) J. Biol. Chem. 267:9307–9314.

Lawrence, J. et al. (1989) Cell 57:493–502.

Lion, T. and O. Haas. (1990) Anal. Blochem. 188:335–337.

Mannino, R. and S. Gould-Fogerite (1988) BioTechniques 6:682–690.

Moore, S. and R. Fishel (1990) J. Biol. Chem. 265:11108–11117.

Pinkel, D. et al. (1986) Proc. Nat. Acad. Sci. 83:2934–2938.

Radding, C. (1989) Blochim. Biophys. Acta 1008:131–145.

Radding, C. (1991) J. Biol. Chem., 266:5355–5358.

Ratajczak, M. et al. (1992) Proc. Nat. Acad. Sci. 89:11823–11827.

Sauer, B. and N. Henderson (1989) Nucleic Acids Res. 17:147–161.

Schowalter, D. and S. Sommer (1989) Anal. Biochem. 177:90–94.

Shigekawa, K. and W. Dower (1988) BioTechniques 6:742–751.

Singer, R. et al. (1986) BioTechniques 4:230–250.

Tan, W. et al. (1992) Science 258:778–781.

Thomas, K. and M. Capecchi (1987) Cell 51:503–512.

Wagner, E. et al. (1992) Proc. Nat. Acad. Sci. 89:6099–6103.

BACKGROUND OF THE INVENTION

Transformation is the integration into and expression of foreign DNA into a host cell. Other terms of art include DNA transfer or transfection of foreign DNA, followed by the stable incorporation of the DNA into a host cell genome. Because transformation can alter gene function, transformation can be utilized for gene therapy. Defective genes can be altered or corrected by the inactivation or replacement of mutant gene sequences. For example, expression of a gene sequence that allows the production of deleterious proteins may be curtailed by blocking the gene's promotor. Or, a defective gene sequence may be corrected by replacing it or by supplying missing bases.

Transgenic animals that have been transformed to carry human genes have become important models for in vivo study of human genetic disease. Gene defects can be established in these animals by inserting gene mutations, and then can be studied and treated by gene therapy. For example, recently developed transgenic mice carrying defective cystic fibrosus (CF) genes are being used as models that approximate human CF symptoms, and to study combinations of drugs that can be used for CF treatment (Dorin et al., 1992). In another research project, leukemic human hematopoiesis has been established in severe combined immunodeficiency, (SCID) mice to provide an in vivo model for the administration of therapeutic treatments for leukemia. (Ratajczak et al., 1992)

Gene therapy promises to become a technology of choice for treating human genetic diseases as more knowledge is gained of the molecular biology and pathology of genetic disorders, and as safe, efficacious gene transfer techniques are developed. As of October, 1992, thirty-seven gene therapy experiments had been approved worldwide. (Science 258:744) The National Institutes of Health have authorized a number of human gene therapy experiments in which a patient's own cells are transformed and returned to the patient to combat genetically derived disease. Among these experiments, adenosine deaminase (ADA) deficiency is being treated by using a retroviral vector to deliver and insert into the patients' white blood cells (which have been placed in culture) a normal ADA gene. Additional gene therapy trials underway include transformation of cells that have been taken from patients with ovarian cancer or cutaneous malignant melanoma. In one research project, genetically engineered viruses containing foreign genes are injected directly into patients' non-small-cell lung cancer tumors. At present "defective" (inactivated) viral vectors are used in the majority of gone therapy procedures. Somatic cell gone therapy has rather low efficiency, is not permanent, and usually must be repeated as, in time, transformed cells die or lose their effectiveness. A major goal of the number of researchers and biotechnology companies (including Systemics Corp.; CellPro, Inc.; Applied Immune Sciences, Inc.; Haemonetics Corp.; Baxter International; and Imclone Systems, Inc.) is the successful culture and transformation of human long-lived pluripotent or totipotent cells for sustained expression of introduced therapeutic genes (Dai et al., 1992).

Diagnosis of aberrant genetic conformation(s) and/or disease states in fixed tissues, cells, and nuclei isolated from cells can be accomplished by standard in situ hybridization (ISH) techniques for which there are numerous published protocols (Pinkel et al., 1986; Lawrence et al., 1989; Singer et al., 1986; Kallioniemi et al., 1992). Both isotopic and non-isotopic ISH have become important methods for identification of malignant cells and for human genome research. Although ISH results can be highly specific, commonly used ISH techniques have many disadvantages, including exacting fixation and storage requirements for individual cell and tissue types, lengthy probe incubation times, complex blocking, reporter processing and washing procedures, and tedious amplification protocols, as well as the need for access to state-of-the art microscopes and related equipment for analysis of results. In addition, high background sometimes resulting from the considerable manipulation (which may cause artifacts) of fixed cells during ISH treatments may make accurate interpretation of results difficult or impossible.

The method of the invention employs the specific catalytic activity of RecA protein (derived from the gram-negative prokaryote *Escherischia coli*) which was discovered about 28 years ago (Clark and Margulies, 1965). In in vitro homologous recombination assays it was learned that RecA protein can mediate both pairing and strand exchange between appropriate DNA molecules (for reviews see Kowalczykowski, 1991, Radding, 1989, 1991; also see Golub et al., 1992). More recently it was reported that in addition to DNA-DNA hybridization, RNA-DNA hybridization can be promoted by RecA protein: RecA protein coated single-stranded DNA (ssDNA) can recognize complimentarity with naked RNA (Kirkpatrick and Radding, 1992; Kirkpatrick et al., 1992).

Other proteins have been shown to catalyze strand-transfer reactions with results similar to RecA protein's, and it is anticipated that, among these prokaryotic proteins such as RecR from *Bacillus subtilis* (Alonso et al, 1993), and eukaryotic proteins such as STP from *Saccharomyces cerevisiae* (Hamatake et al., 1989), or RecA-like activity from *S. cerevisiae* (Kolodner et al., 1987), or Rec1 from *Ustilago maydis* (Kemic and Holloman, 1986) or RecA homolog in plastids in the plant *Aradidopsis thaliana* (Cerutti et al, 1992), or a protein from human cells which has homologous pairing activity (Moore and Fishel, 1990), or other proteins as yet undescribed may prove to be effective mediators of recombinant hybridization. One or more of these proteins may be found to function in pathways similar to RecA's and may provide catalytic activity which is analogous to RecA's for the purposes of this invention.

Although RecA has proved to be a useful in probing for a predetermined DNA sequence in the genome of a given cell, whether naturally occurring or introduced by recombinant techniques, its usefulness is largely limited to in vitro studies wherein the cells have already been fixed, and thus are no longer capable of reproduction. In one particular instance, RecA has been mentioned in connection with the use of viral capsids to introduce foreign DNA into a cell capable of being infected by the viral capsid. As set forth in detail in U.S. Pat. No. 4,950,599 to Bertling, polyoma or polyoma-like capsids are used to encapsulate an exogenous DNA sequence, followed by contacting the polyoma capsid to permissive cells, whereupon the exogenous DNA is taken up by the cell and exchanged with a substantially homologous DNA sequence already present in the cell. Bertling further mentions that the DNA should be combined with some sort of DNA binding protein to promote homologous recombination events, although such combination is not necessary to practicing the technique as broadly disclosed in the patent. Among the several such binding proteins mentioned is RecA. Unfortunately, the techniques discussed by Bertling rely on the use of an infecting vector. It will be understood by one skilled in the art that the construction of the infecting vector-DNA combination is a time-consuming, fairly labor intensive process that involves a significant loss of both convenience and time in order to achieve transformation of a given cell.

In view of techniques currently utilized for the detection of specific gene sequences in cells there is clear need for a simple and reliable in vivo method. There is also clearly a need for a simple, reliable method for in vivo transformation of living cells without excessive physical or chemical disruption of cell membranes, and which does not involve infectious agents or other vectors that may have a deleterious effect on the cells to be transformed.

SUMMARY OF THE INVENTION

In view of the deficiencies and limitations of existing techniques, the general objects of the present invention are therefore to provide a simple, efficient method of detection of specific gene sequences in cells; to provide for in vivo regulation of cellular genes by inactivating or altering specific nucleic acid sequences; and to provide for in vivo transformation of cells by introducing and integrating foreign gene sequences into the chromosomes of the recipient cells.

The present invention achieves these objects by providing a simple, convenient method for background-free detection of the presence of specific nucleic acid sequences in cells. Further, the invention provides a simple, non-deleterious method for transforming cells without resort to the harsh physical manipulations or vectors used in current transformation techniques.

In the method of the invention, cells are removed from the substrate on which they are growing or from the growth media in which they are suspended and placed in an Eppendorf tube. Probe complexes containing single stranded DNA probes that have been coated with RecA protein in the presence of ATPγS and that are complimentary to one or both of the strands of a targeted duplex nucleic acid sequence or to a targeted single stranded nucleic acid sequence are added to the intact living cells. The complexed RecA-coated probe may be unlabeled; or it may be labeled with a directly detectable reporter such as a radiolabel, enzyme or fluorescent tag; or the probe may be labeled with a ligand, such as biotin, digoxigenin or alkaline phosphatase that is subsequently reacted with a detectable reporter molecule specific for the ligand. The cells are then incubated with the probe complex at physiological temperature within a $CO_2$ incubator or in a waterbath. Following incubation unbound probe components are removed by washing.

Cells that have been treated with probe complexes may be replated or resuspended and replaced in a $CO_2$ incubator. Cells treated with labeled probe complexes may be fixed immediately. Depending on the purpose of the experiment and regardless of whether or not the probe complexes contain labeled probe, treated cells may be replaced in a $CO_2$ incubator and allowed to grow. Huijzer and Smerdon (1992) reported that biotinyl-11-deoxyuridine triphosphate incorporated into DNA in living human fibroblasts in UV radiation excision-repair assays is not totally removed for more than 72 hours, and that the biotin tag does not appear to prevent the folding of nascent repair patches into native nucleosome structures and does not interfere with cell division. In assays conducted by the method of the invention cells treated with biotin labeled probe divided successfully and daughter cells incorporated biotin label.

If the purpose of the experiment is diagnostic, labeled probe-treated cells may be appropriately fixed and processed immediately or processed immediately without fixation to determine if a specific gene sequence is present. Alternatively, for purposes such as for kinetic assays, cells treated with a reporter or ligand labeled probe may be removed from culture periodically for detection of bound probe and/or to determine if probe binding is transient or stable. Cells may also be treated in vivo with more than one probe for processing and detection of recombination, each probe having been labeled with a different reporter or ligand. Depending on the type(s) of labeling and processing required for detection of recombination, probed cells are examined by phase or fluorescence microscopy, by confocal laser scanning microscopy, or using various combinations of these microscopy techniques. In some experiments fluorescent activated cell sorting (FACS) is appropriate.

When the purpose of the experiment is to obtain numbers of transformed cells, several groups of probe-treated cells are placed in the $CO_2$ incubator and allowed to multiply so that examples from different groups can be tested to identify transformants. Testing may be performed by PCR. Other methods may be useful for the selection of transformants. For example, a submicrometer sensor might be used to measure chemical concentrations or pH profiles in cellular compartments of individual cells (Tan et al., 1992) to detect those which have been altered by transformation. Selected transformants are expanded and are monitored to determine if transformation is stable and is passed on consistently to daughter cells.

Under the method of the invention certain mammalian cells may be grown in primary culture, treated for transformation, selected for and identified as homologous transformants, isolated, expanded, and reintroduced into the donor as "vector cells" carrying the desired gene sequence(s). Expression of deleterious gene sequences can be blocked by antisense oligonucleotide probes that interfere with synthesis of undesirable proteins. In vivo diagnostic in situ detection of specific gene sequences (as well as identification of transformants) can be performed using the method's diagnostic protocols. The method of the invention may allow the transformation of differentiated cells in situ rather than in primary (and secondary) culture. Eventually, when it becomes possible to culture and expand original progenitor stem cells, a primary focus of intense research (see Gutierrez-Ramos and Palacios, 1992), the method will greatly extend diagnostic and transformation possibilities, and allow the prolongation of duration of therapeutic effects.

The method is convenient for in vivo determination of the presence (or absence) of a known, specific target sequence in a nucleic acid contained in a living cell. Further, the method is suitable for blocking, altering, or changing by transformation a known, specific target nucleic acid sequence in a living cell.

The method of the invention differs from existing transformation techniques, in that the method does not alter cellular integrity. Rather, it permits treatment of cells at near physiological conditions. The numbers of cells which can be processed with transforming components are not limited by labor-intensive mechanical penetration as in microinjection (Folger et al., 1982), and the method does not rely on electrically facilitated transient rupture of cell membranes as in electroporation (Shigekawa and Dower, 1988; Dorin et al., 1992). Nor is the method based on the uptake of calcium phosphate/DNA co-precipitates (Graham, and van de Eb, 1973), or lipid encapsulation (lipofection) (Mannino and Gould-Fogerite, 1988), and the method does not depend on chemical modification of or alteration of or impairment of cell morphology which occurs when plasma membrane permeabilization procedures are used. Many of the transformation procedures described in the above references are used in combination and/or rely on viral or other vectors. (For further examples see: Wagner et al., 1992; Davis et al., 1992; Sauer and Henderson, 1989; Cotten et al., 1992; Thomas and Capecchi, 1987; La Salle, et al., 1993). Rather, the method of this invention allows treatment of entire cells without mechanical and/or chemical manipulation and does not involve the use of viral or bacterial or other transformation vectors.

The method of this invention establishes a simple, effective technique for efficient, non-random, in vivo integration of foreign nucleic acid sequences into chromosomes for elucidation of gene structure and function. The method has excellent potential for safe, reliable gene therapy. Because probed cells are not physically damaged or altered, and because viral vectors, which have not been proven to be entirely safe, are not used, the method is eminently suitable for human gene therapy. Human cells which may be successfully removed, cultured, tested, transformed and replaced by the method for the invention, include cells from bone marrow, skin, myoblasts, fibroblasts, endothelial cells, hepatocytes, nerve cells, T lymphocytes. Optimal procedures may be established to place transformed cells directly into specific areas in the body, for example into tumors, blood vessels, and lungs. The method is appropriate for use with both suspended and adherent cells, and does not limit the number of cells which can be treated. The method allows background-free, in vivo determination of the presence or absence of specific nucleic acid sequences, and thus is ideal for exacting diagnostic applications.

The transformation and diagnostic method embodied in this invention targets gene sequences for recombination in vivo in fully intact cells. The passage of probe components into cells may be driven by ion gradients, however the mechanism(s) of passage or transport of the transforming agents both through the plasma membrane and into the nucleus is (are) not known. In the method of the invention recombination may take place most readily during cell division when the nuclear membrane is disrupted.

The method of the invention is based on RecA-mediated pairing and strand exchange reactions, in which RecA protein in the presence of ATPγS is allowed to coat single-stranded nucleic acid probe sequences, forming stable helical presynaptic filaments. In the in vitro experiments on which the method of this invention is based, the presynaptic filaments are added to naked duplex helical DNA, forming non-homologously paired intermediates, coaggregates of single-stranded and double-stranded DNA in nucleoprotein networks whose exact structure is not yet known. Homologous alignment and strand exchange then take place in a manner not fully understood (Kowalczykowski, 1991).

These and other objects and advantages of the invention will become more fully apparent when the following detailed description of the invention is read in conjunction with the accompanying figures.

DETAILED DESCRIPTION OF THE INVENTION

I. In Vivo Hybridization Method

Figure 1A:
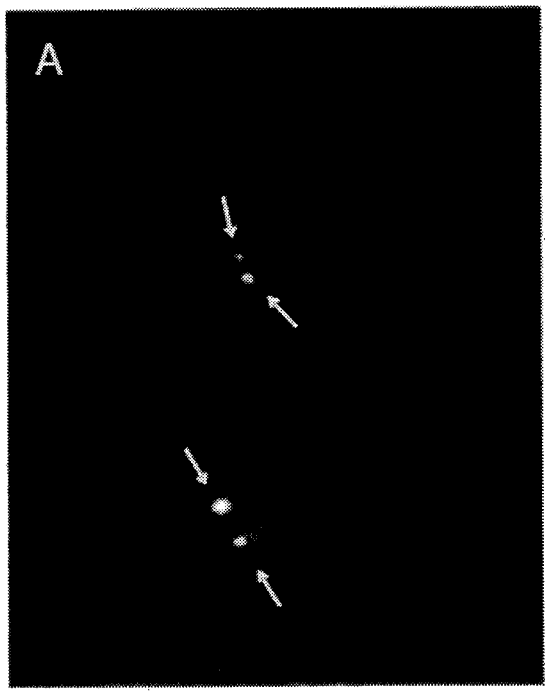
FIGS. 1A, 1B, and 1C are polaroid photomicrographs showing fluorescent reporter label in HEp-2 cells that were incubated in vivo with a biotinylated probe to Chromosome 17 p53 gene, returned to the $CO_2$ incubator, and FITC-avidin-treated 22 hours later.
Figure 1B:
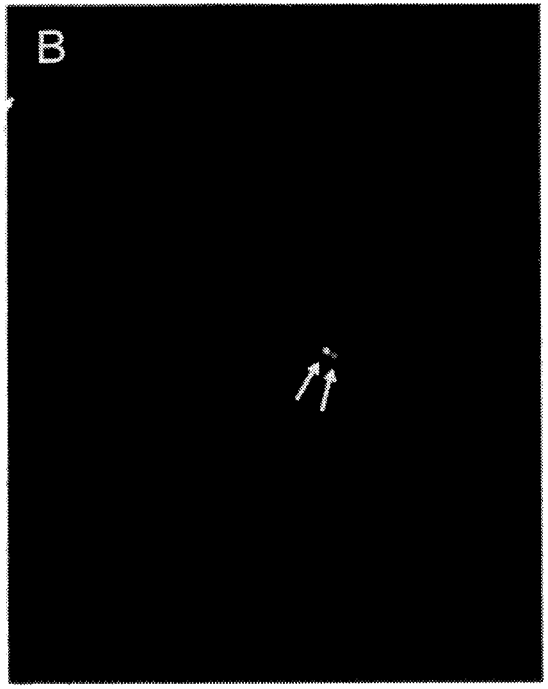
Figure 1C:
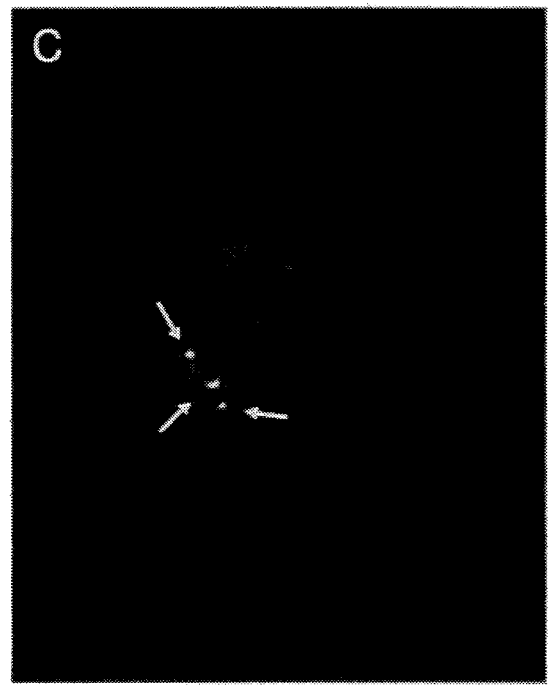
Figure 1D:
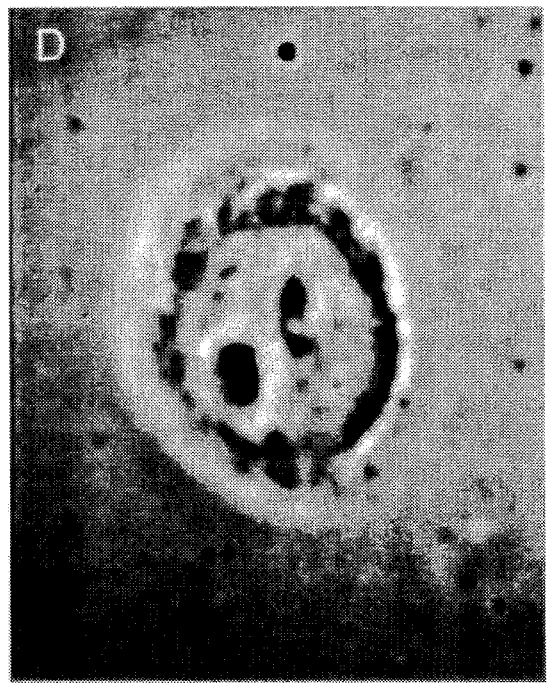
FIG. 1D is a polaroid photomicrograph showing a phase image of the cell in FIG. 1C without changing focus.

This section outlines the basic protocols for in vivo transformation and diagnostics in accordance with the method of the invention, as applied to various cell types, including parasites and sperm.

A. Preparation of cells for in vivo nucleic acid sequence detection, blocking, alteration, and transformation The method of the invention is designed for in vivo complementary-base pair hybridization to duplex nucleic acid target sequence in cells. Duplex target sequences are typically DNA/DNA sequences, but may be DNA/RNA (or, possibly, double-stranded RNA elements), and include double-stranded or single-stranded nucleic acid sequences associated with viral, bacterial or parasitic pathogens.

Shortly before in vivo treatment with nucleic acid probe mixture, cells growing in petri dishes are trypsinized, gently washed with phosphate buffered saline (PBS), and pelleted at low speed in an Eppendorf tube, or cells growing in suspension are pelleted, gently washed with PBS, and repelleted in an Eppendorf tube. The cells are quickly rinsed with incubation buffer immediately prior to mixing with prepared nucleic acid probe complexes.

B. Preparation and Labeling of Nucleic Acid Probes

Probes used in the method of the invention are single-stranded and are complementary to one or both strands of the target duplex nucleic acid(s). Duplex probes are denatured to separate them into single strands. Probes for strand exchange are ideally between 200 and 700 bases long (however shorter or longer probes may also function), and are preferably more than 90% homologous with their target sequence(s). Some probes to nucleic acid sequences of disease-carrying organisms, such as to Hepatitis B, are commercially available. Probes may be constructed by oligonucleotide synthesis, and, if necessary, by ligating subfragments. Constructed probes may be amplified by polymerase chain reaction (PCR). Specific probe sequences may be obtained by means of restriction enzyme digestion of viruses, plasmids, cosmids, or other vectors, followed by electrophoretic separation of cut fragments and electroelution. These probe sequences may be amplified by PCR.

Probes are labeled with a reporter or ligand when they are to be used for diagnostic detection of target sequences and/or for detection of transformation. The three main enzymatic techniques for labeling DNA or constructed probes (prepared by oligonucleotide synthesis, PCR, etc.) are nick translation, random priming, and PCR. There are also several chemical and photochemical labeling methods suitable for the method of this invention. Radioactive molecules for direct (e.g., autoradiography) and nonradioactive reporter molecules for direct and indirect detection systems may be used. For non-isotopic labeling, sensitive, direct reporter groups are covalently linked for probes. These reporter groups include fluorescent dyes and marker enzymes. For indirect, non-isotopic labeling a modification group (such as biotin or digoxigenin) is introduced into the probe that is bound to a detectable reporter group following incubation of probe with cells. Several other probe labeling and detection schemes have been described (Kricka, 1992).

C. Assembly Of Nucleic Acid Targeting Components

In a typical standard assay probe is placed into a 0.5 ml Eppendorf tube, denatured in a 100° C. heat block, chilled in an ice bath, and added to a mixture containing buffer, magnesium acetate, ATPγS, and RecA. The assembled probe mixture is incubated in a water bath at 37° C. for 12 to 15 minutes and is completed by a final addition of magnesium acetate. Additional or different probe mixture components and/or modifications may be effectively employed depending on the type of cell to be diagnosed and/or transformed, intracellular ionic concentration, and the particular circumstances of the assay. The method of the invention is not restricted to the specific components and concentrations of components described both above and in the examples which follow.

In the method of the invention concentrations of probe mixture components are empirical; working ratios are determined experimentally. Depending on the type of cell being treated and the concentration(s) of target sequence(s), it is anticipated that it may be advantageous to titrate components such as ATPγS and RecA, and to experiment with less (or more) nanograms of probe and/or vary buffer components. Since the amount of probe mixture that can be used successfully with a single cell type has been shown to be variable (see examples below) the ratios of probe complex components to each other are variable. In in vitro assays involving RecA polymerization, $Mg_2^+$ concentration is usually substantially increased after polymerization (Cheng et al., 1988). Based on in vivo RecA mediated DNA strand exchange assays using polyvinyl alcohol and polyethylene glycol as volume-occupying agents to simulate the in vivo effects of macromolecular crowding Lavery and Kowalczykowski (1992) suggested "that a low in vivo magnesium ion concentration would not compromise the ability of RecA protein to promote recombination reactions". In similar RecA catalyzed in vitro assays, $Mg_2^+$ concentrations from 8 to 20 mM were shown to have about the same effect (Koob, 1992).

D. Incubation of Probe Mixture with Living Cells

Immediately following the final addition of magnesium acetate the completed probe complex is mixed into approximately $1.25-2.00\times10^6$ cells, which have been prepared as outlined in Section A above. Eppendorf tubes containing the cell-probe mixture may be placed either in a 37° C. $CO_2$ incubator or in a 37° C. waterbath incubated for between 30 minutes and 1 hour.

E. Washing and Processing of Treated Cells for Diagnostic Purposes or for Detection of Transformation In a typical assay and for the purpose of immediate diagnostic analysis of results, cells that have been incubated in vivo with labeled probe mixture (label is often biotin) are briefly washed with PBS and incubated in the dark at room temperature with reporter often fluorescinated avidin in blocking solution. Cells are then rinsed with sodium citrate washes and placed on slides with a mounting medium (formula in Example 2, below) which reduces photobleaching during viewing under a fluorescence microscope.

When analysis of results is to be delayed, for example for evaluation of the kinetics of probe binding to nucleic acid target(s) or for assessment of the stability of homologous recombination, labeled probe-treated cells are returned in petri plates (or flasks where cells are grown in suspension) to the $CO_2$ incubator after having been washed free of probe mixture with PBS and having been mixed into a combination of cell-free conditioned and fresh complete growth media.

Cells that have been incubated with unlabeled probe complex are returned to the $CO_2$ incubator after washing and addition of conditioned and fresh growth media.

Depending on the purpose of the experiment or manner of treatment of cells, at a specified time or at specified times following incubation with probe-complex treated cells are appropriately processed. For immediate detection of the presence of label (indicating recombination) cells are treated as outlined in the first paragraph in Section E above. Or cells are washed in PBS and fixed. Adherent cells in petri plates may be fixed for 10 minutes with 100% ice cold ethanol. Or, adherent cells may be trypsinized and fixed in suspension by gentle vortexing in 100% ice cold ethanol or methanol. Fixed cells may then be frozen for later detection of probe binding, or the cells may be processed immediately. For detection of biotinylated probe in fixed cells that have been frozen, the cells are incubated with bovine serum albumin (BSA) in PBS for 30 minutes, rinsed two times with PBS, then incubated with FITC-avidin reporter in the dark at room temperature for 30 minutes, followed by rinsing with sodium citrate washes. Observation of the presence of fluorescent label is performed by preparing cells in antifade mounting media and viewing the cells under a fluorescence microscope. The protocols outlined above can be adapted for use with different reporter systems.

F. Processing Of Probe Complex Treated Cells for Selection and Expansion of Transformants Protocols for the selection and expansion of transformants will vary depending on the type of cell treated for transformation. It is anticipated that a combination of techniques will be employed in order to ascertain the stability of transformation, the percentage of cells stably transformed, and to accomplish expansion of transformants. For example, both unlabeled and labeled (isotopically or nonisotopically) probe complex treatment of cells may be performed in one experiment. Cells treated with labeled probe complexes can be processed for detection and quantification of transformation. PCR may be used to examine the extent of transformation in separate expanded cell colonies derived from cells which were treated for transformation with unlabeled probe complexes. The colonies which are composed of transformed cells can be isolated and further expanded.

II. Applications

A diagnostic application of the invention is the in vivo targeting in a chromosome of a specific gene, or of a sequence within a gene, or of a regulatory sequence. The target may be a sequence within a gene that is thought to be or that is known to be potentially damaging to an organism, such as an oncogene or proto-oncogene, or the target may be a sequence within a regulatory sequence that prevents the synthesis of a normal gene product or a sequence within a regulatory sequence that allows the synthesis of a deleterious gene product. The target may be a sequence that allows the accurate assignment of the position of a marker in a chromosome within a map of the chromosome. Alternatively, the target may be a repetitive sequence in the DNA of a chromosome whose topology changes during the cell cycle; a viral sequence; or a transformed sequence in a cell transformed by the method of the invention. Following in vivo incubation with probe-complex treated cells may be processed at once (in vivo or in vitro) for diagnostic detection of probe complex targeting, or the cells may be replaced in the $CO_2$ incubator and processed later for detection of targeted sequences.

The nucleic acid diagnostic probes may be chemically synthesized where gene sequences are known, or probes may be derived from gene products, or may be obtained from plasmids, cosmids, viruses or other vectors, or from human genomic libraries. Purification by electrophoresis, electroelution, and ethanol precipitation, or elution through a column may be suitable for producing some probe complexes. PCR may be used to amplify, and also to label probes' sequences, sometimes simultaneously (Lion and Haas, 1990; Schowalter and Soreruer, 1989). Use of multiple labeled probe complexes is an option. Signal from labeled probe complexes bound to target(s) may be amplified by "sandwich" techniques (for example, amplification of FITC-avidin label by incubation of probe-treated cells with biotinylated goat anti-avidin antibody followed by incubation with FITC-avidin) to augment signal.

For ordering of genes on chromosomes, cells in culture may be staged and premitotic cells isolated and incubated in vivo with a probe mixture containing biotinylated probe to one gene sequence combined with a second probe mixture containing digoxigenin-labeled probe to a sequence in a second gene thought or known to be close to the first gene. Cells incubated with the probe mixtures can then be incubated with colcemid to promote metaphase, then fixed on slides for ISH, and then treated with appropriate reporters (for instance with FITC labeled avidin for attachment to biotin and with gold labeled antidigoxigenin antibody for attachment to digoxigenin) making it possible to visualize the position of the two genes in relation to each other, as well as to the chromosome's centromere. Likewise cellular mutational events may be identified by cytogenic analysis, for example by comparing the ratios of probe hybridization signals in cells within a tumor with probe hybridization signals in reference to "normal cells" exterior to the tumor.

In the transformation application of the invention, where it is undesirable for labeled reporter molecules to be incorporated as a result of the procedure, cells are targeted in vivo with appropriate probe complexes that are unlabeled. The absence/presence of transitory or stable transformation can be ascertained by allowing the treated cells to continue growing after treatment with the probe complex, thereafter periodically testing some of the cells for evidence of transformation, using a labeled probe complex under the diagnostic method protocols of the invention. If a transformation procedure involves the blocking of the synthesis of a gene product or involves the repair of a gene sequence in order to allow synthesis of a gene product, it will sometimes be possible to assess transformation success by detecting the absence or presence of the gene product, for example by using antibodies against the product (antigen) or by the use of PCR and electrophoretic measurements or by biochemical means.

An example of a therapeutic embodiment of the invention is the blocking of a gene promotor sequence, thereby preventing initiation and transcription of a deleterious gene product. The cells to undergo transformation by means of RecA-mediated homologous recombination in which the targeted sequence is blocked are removed from an individual and placed into culture. Following transformation treatment, cells shown to be stably transformed are expanded and returned to the donor. In a variation on this theme "wrong" or missing bases are replaced or added to genes to "correct" them. It is possible that protocols may be developed that will allow transformation by the method of the invention of differentiated cells (such as keratinocytes) into manufacturers of an essential protein that the cells would otherwise not produce. The transformed cells would then be returned to the individual (in this example possibly by grafting) to help supply the missing protein.

The following examples illustrate procedures for preparing and using probe complexes according to the method of the invention. The examples are intended to illustrate, but not limit, the scope of the invention.

EXPERIMENTAL

EXAMPLE 1: Preparation of Probe Complex 100 nanograms (10 µl) of biotinylated Chromosome 17 p53 gene probe (ONCOR, Gaithersburg, Md.) was mixed with 6 µl of sterile double distilled $H_2O$ in a sterile 0.5 ml Eppendorf tube, denatured at 100° C. in a heat block for 5 minutes, then immediately placed in an ice bath for approximately 45 seconds to prevent renaturation and/or self-aggregation. The iced probe was briefly centrifuged at 0° C. for consolidation at the bottom of the tube and added at once to a sterile 0.5 µl tube containing the following components assembled in the order listed: 1 µl reaction buffer [20X reaction buffer: 100 mM tris acetate pH 7.5 at 37° C., 20 mM magnesium acetate, 10 mM dithiothreitol, 500 mM sodium acetate, 50% glycerol (after Cheng et al., 1988), 0.75 µl magnesium acetate (20 mM stock), 1.5 mM ATPγS (3.24 mM stock)(Sigma), and 0.75 µl RecA (0.229 mM stock). The probe mixture was incubated in a 37° C. waterbath for 15 minutes, then 0.5 µl magnesium acetate (200 mM stock) was added to increase the $Mg^{2+}$ ionic concentration, stabilizing the reaction. Approximate final molarities of components in the completed 20.5 µl reaction were: 6.59 mM magnesium acetate, 24.39 mM sodium acetate, 0.49 mM DTT, 0.24 mM ATPγS, and 8.39 µM RecA. It should be noted again that the final molarities of several components in a reaction can be varied without compromising results.

EXAMPLE 2: In Vivo Incubation of Cells with Probe Complexes and Detection of Probe Targeting after 22 Hours HEp-2 cells (from larynx epidermoid carcinoma tissue of a human male) were from the American Type Culture Collection (ATCC) CCL 23 cell line. Cells in this line have variable ploidy, and average 2–4 Chromosome 17 chromosome/cell (Chen, 1988). Cells were cultured in petri plates in complete media (DMEM, Whittaker supplemented with 10% Fetal Bovine Serum (FBS), sodium pyruvate and Penstrep® (Gibco) and were grown in a $CO_2$ incubator at 37° C., 7% $CO_2$. Seventy-two hours after seeding of cells, media was removed from the petri plates, centrifuged, and saved. Cells were trypsinized and washed with 1 X PBS. Approximately $1.5\times10^6$ cells in PBS were added to a sterile 0.5 ml Eppendorf tube. The tube was centrifuged at room temperature for 15 seconds at low speed, PBS supernatant removed, and the cells quickly rinsed with 1 X reaction buffer. After brief centrifugation reaction buffer supernatant was removed.

15.5 µl of probe mixture containing 100 nanograms of p53 probe or probe to Chromosome 17 alpha satellite DNA prepared immediately prior to use (as in Example 1) were mixed with the cells incubated in a water bath at 37° C. After one hour the cells were washed with 1 X PBS, resuspended in 500 µl "conditioned" (used) mixed with fresh complete media (1:4) and placed in the center of two 60 millimeter petri plates within grease pencil marked circles. Cotton moistened with sterile dd $H_2O$ was placed in the plates at the edges, and the covered plates loosely wrapped in saran to maintain humidity. After 14 hours incubation attached cells in one plate were tested for 0.4% trypan blue exclusion. Twenty-two hours after reseeding cells were gently washed two times with sterile 1X PBS by using a 1 ml pipetter. 90 µl of 10 µg/ml FITC-avidin (Vector Laboratories, Burlingame) in blocking solution (4X SSC, 0.1% Triton X-100, 5% nonfat dry milk, 2% normal goat serum, pH 7.4) (20X SSC: 3 M NaCl, 0.3 M sodium citrate) was placed on the cells and the cells incubated for 30 minutes in a $CO_2$ incubator. FITC-avidin mixture was removed and the cells rapidly rinsed with 100 µl each of 4X SSC, 4X SSC+ 0.1% Triton X-100, 4X SSC. 10 µl of antifade (to reduce photobleaching during fluorescent microscope evaluation) was used to mount a coverslip over the treated cells. Antifade: 100 mg p-phenylenediamine dihydrochloride (Sigma P1519) is prepared in low light in 10 ml PBS adjusted to pH 8 with 0.5M carbonate-bicarbonate buffer (0.42 g $NaHCO_3$ adjusted to pH 9 with NaOH in 10 ml dd $H_2O$). Cells were examined immediately under fluorescence. There was specific fluorescent signal in many cells showing the presence of targeted p53 gene sequences (FIG. 1) and Chromosome 17 alpha satellite DNA (not shown).

Figure 2:
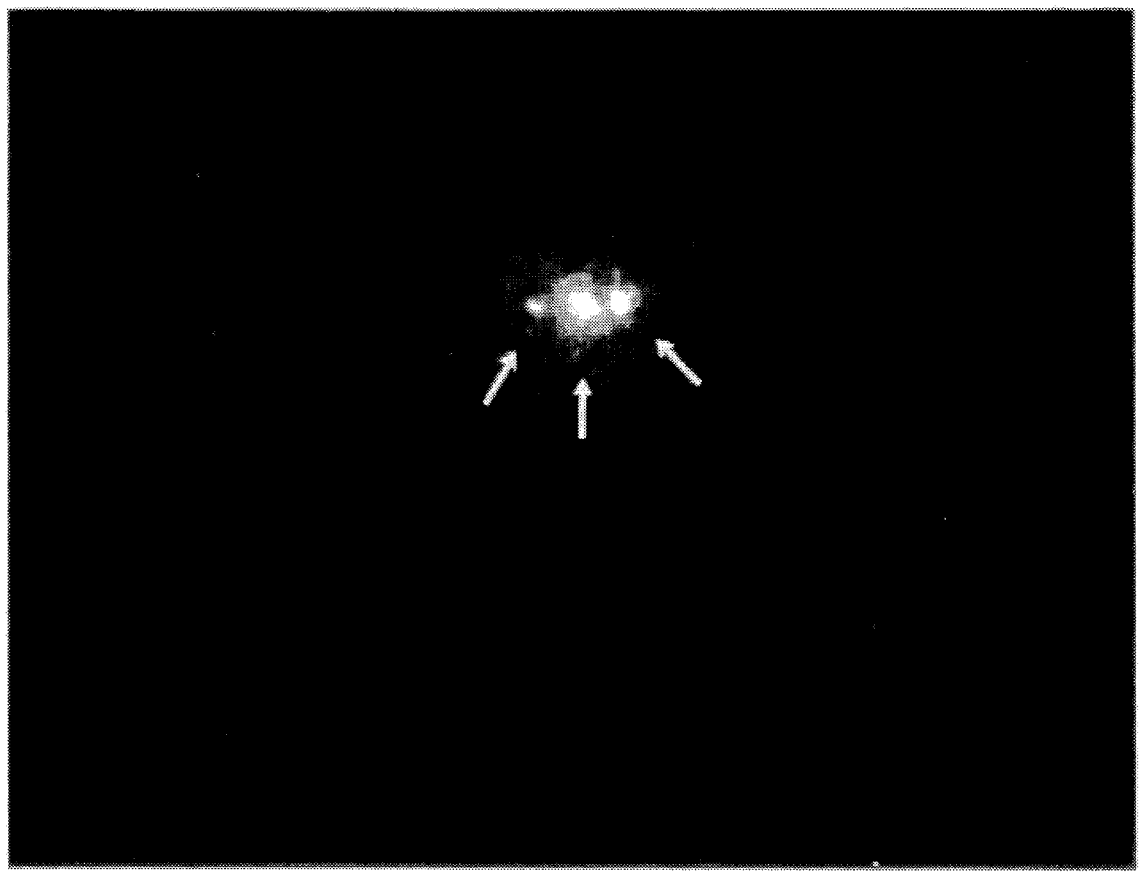
FIG. 2 is a polaroid photomicrograph showing a fluorescent image of a HEp-2 cell that was incubated in vivo with a biotinylated probe to Chromosome 17 alpha satellite DNA and immediately treated with FITC-avidin.

EXAMPLE 3: In Vivo Incubation of Cells with Chromosome 17 Alpha Satellite DNA Probe Followed Immediately by Detection of Probe Targeting Probe mixture and HEp-2 cells were prepared and the cells incubated with 15.0 µl probe as in Examples 1 and 2, with the exception that the cells were treated immediately under the same protocols as in Example 2 without further incubation for detection of gene targeting. FIG. 2 shows a cell with three specific signals marking the alpha satellite sequences of 3 chromosome 17s in the cell.

Figure 3A:
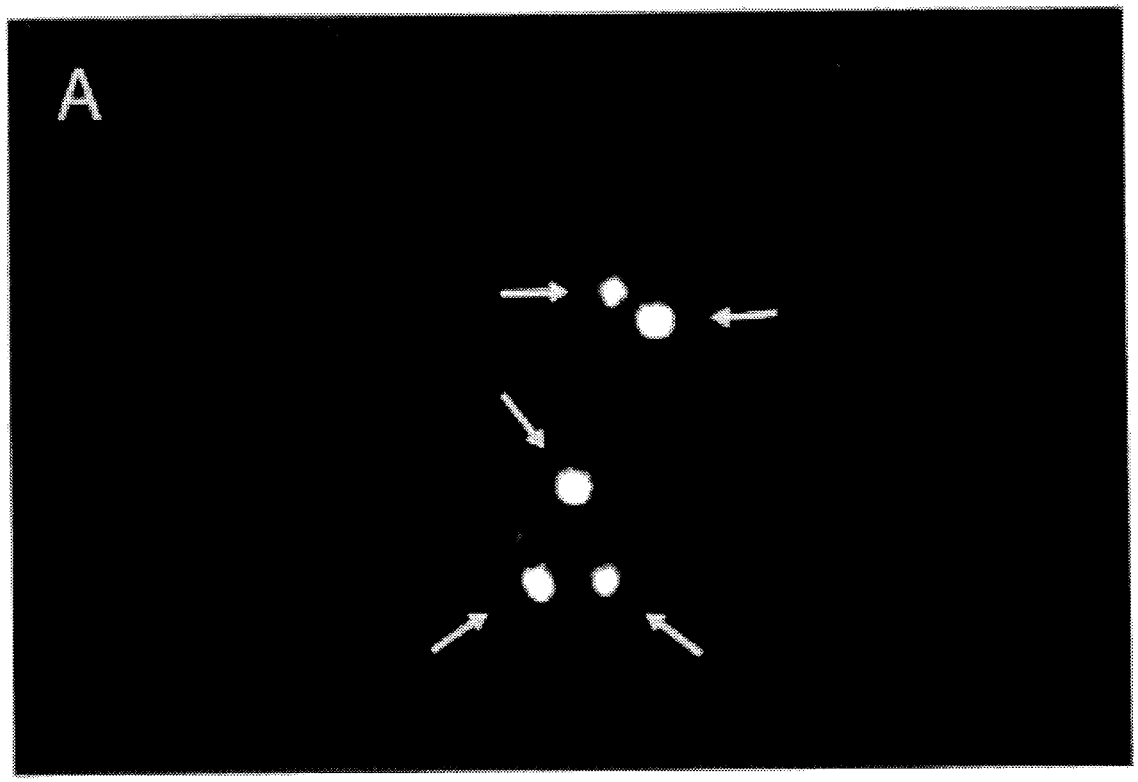
FIGS. 3A and 3B are laser scanning microscope photomicrographs of fluorescent and phase images of a HEp-2 cell incubated in vivo in suspension with biotinylated probe to the P53 gene, then fixed and stained after 16 hours incubation in a $CO_2$ incubator.
Figure 3B:
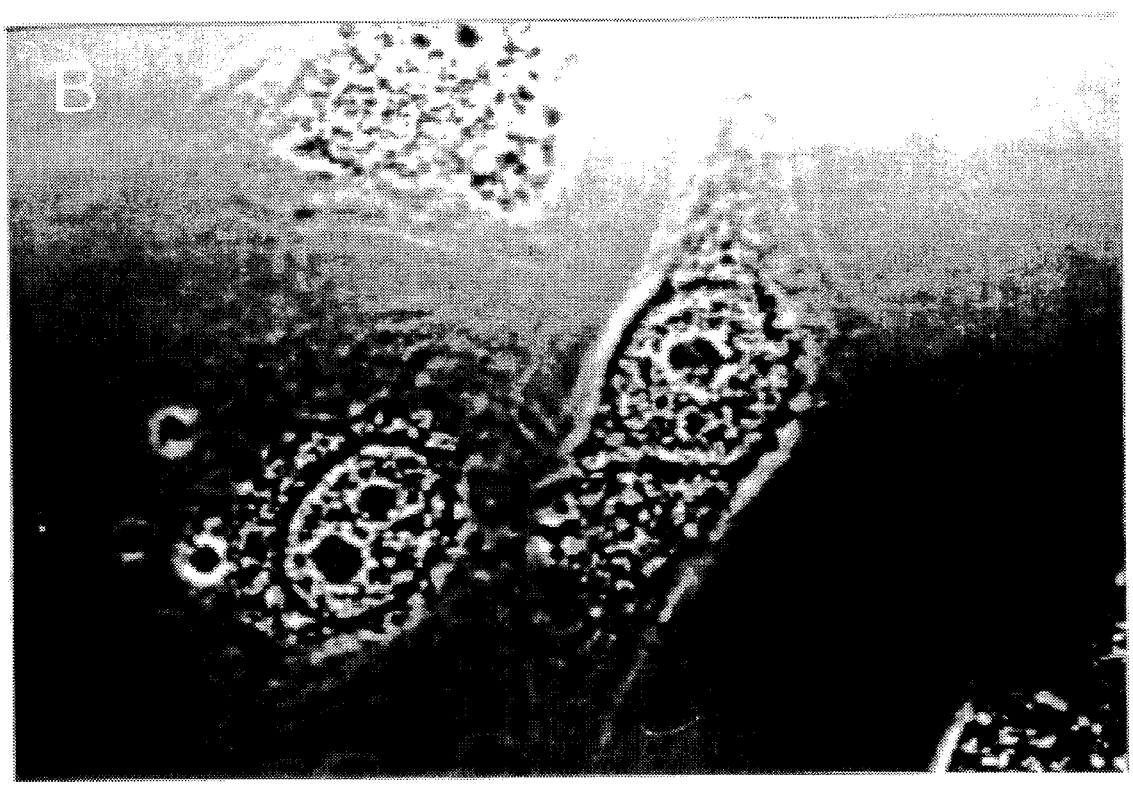
Figure 4A:
FIGS. 4A and 4B are fluorescent microscope photomicrographs and FIGS. 4C and 4D are the phase images respectively of HEp-2 cells from the same experiment described in FIG. 3.
Figure 4B:
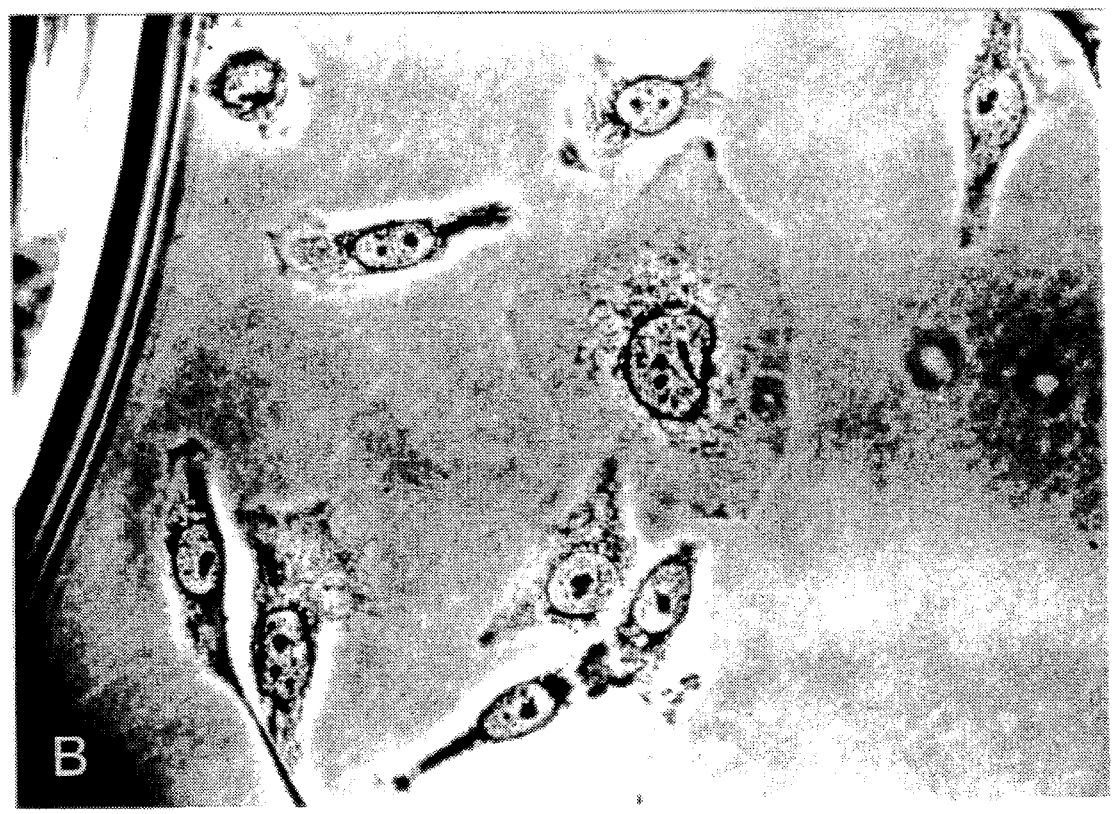
Figure 4C:
Figure 4D:
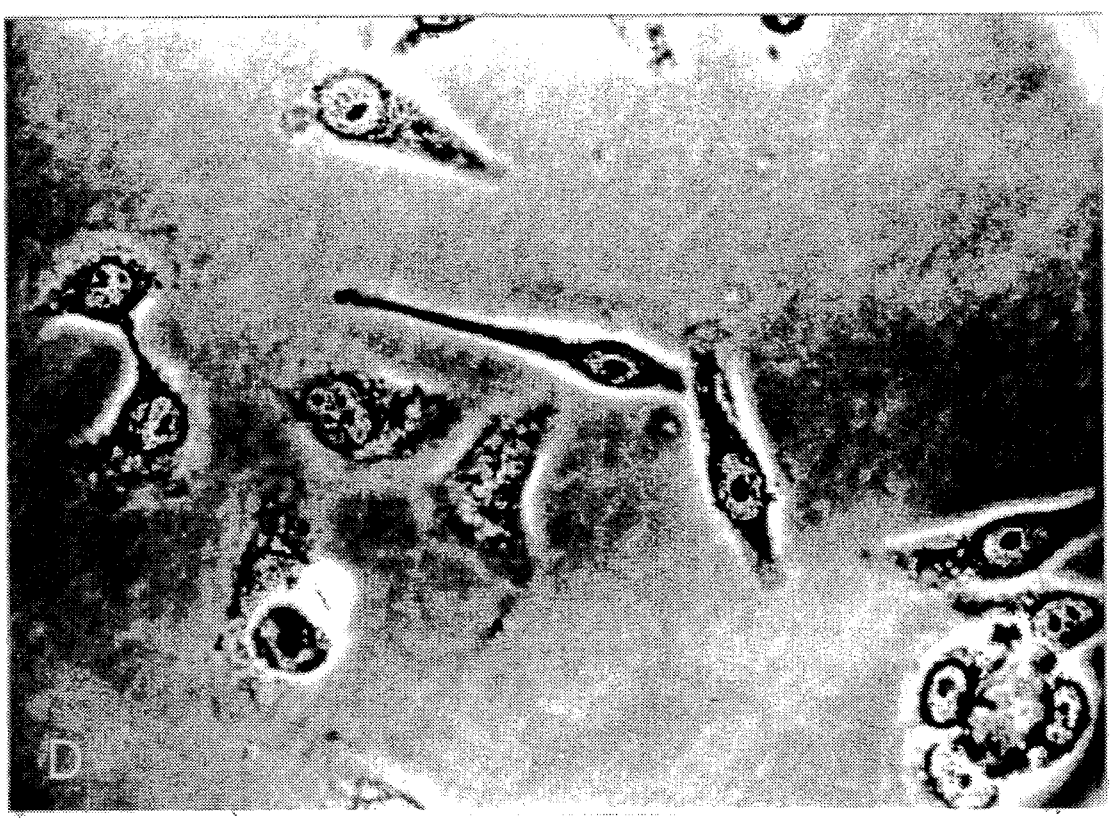
Figure 5A:
FIGS. 5A and 5B are fluorescent microscope photomicrographs and FIGS. 5C and 5D are the phase images respectively of HEp-2 cells incubated in vivo in suspension with biotinylated probe to Chromosome 17 alpha satellite DNA, then fixed and stained after 16 hours incubation in a $CO_2$ incubator.
Figure 5B:
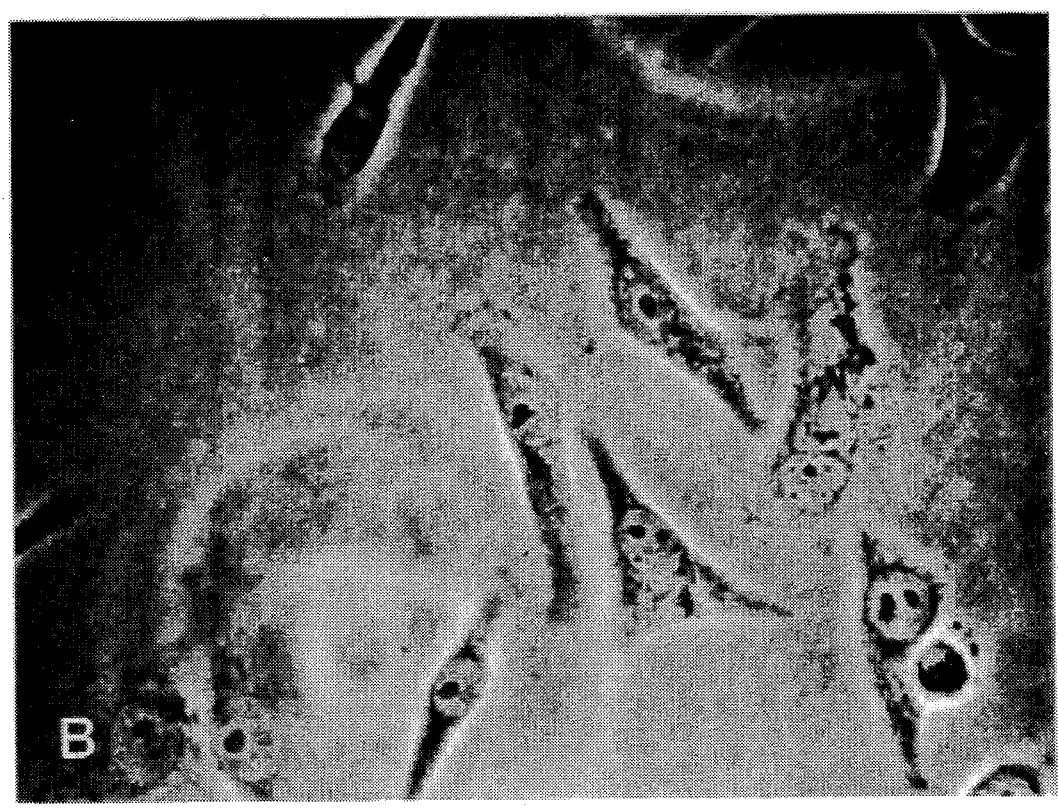
Figure 5C:
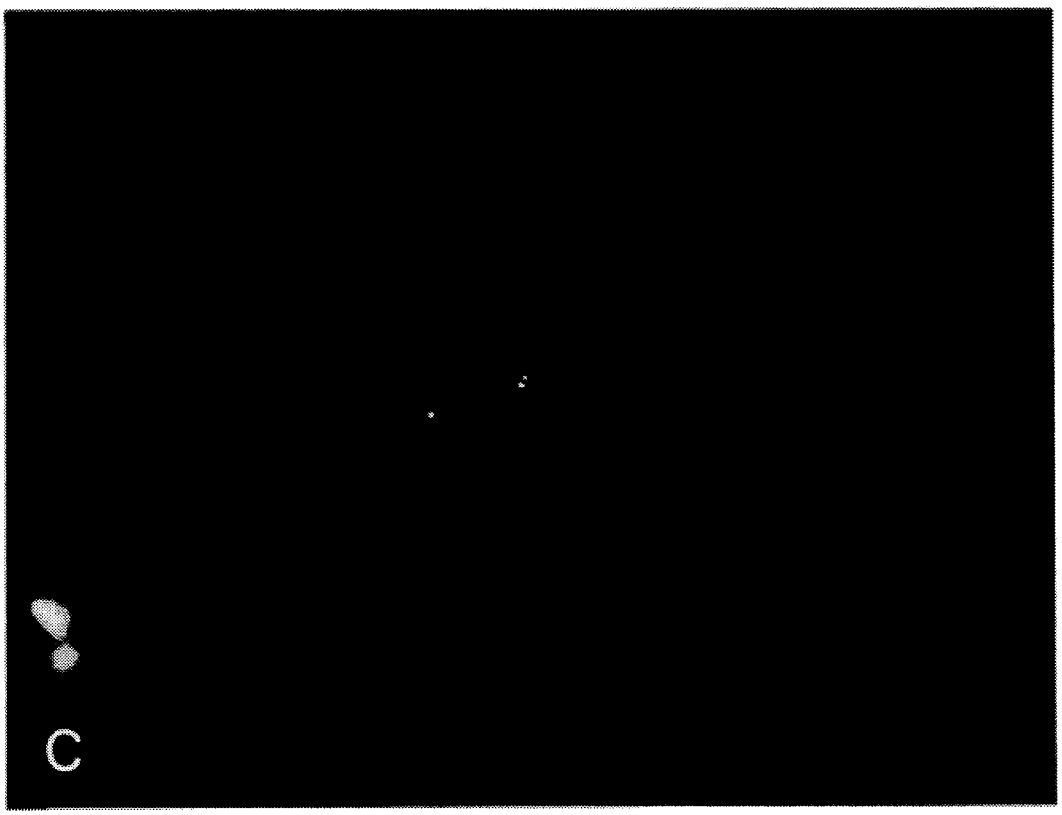
Figure 5D:
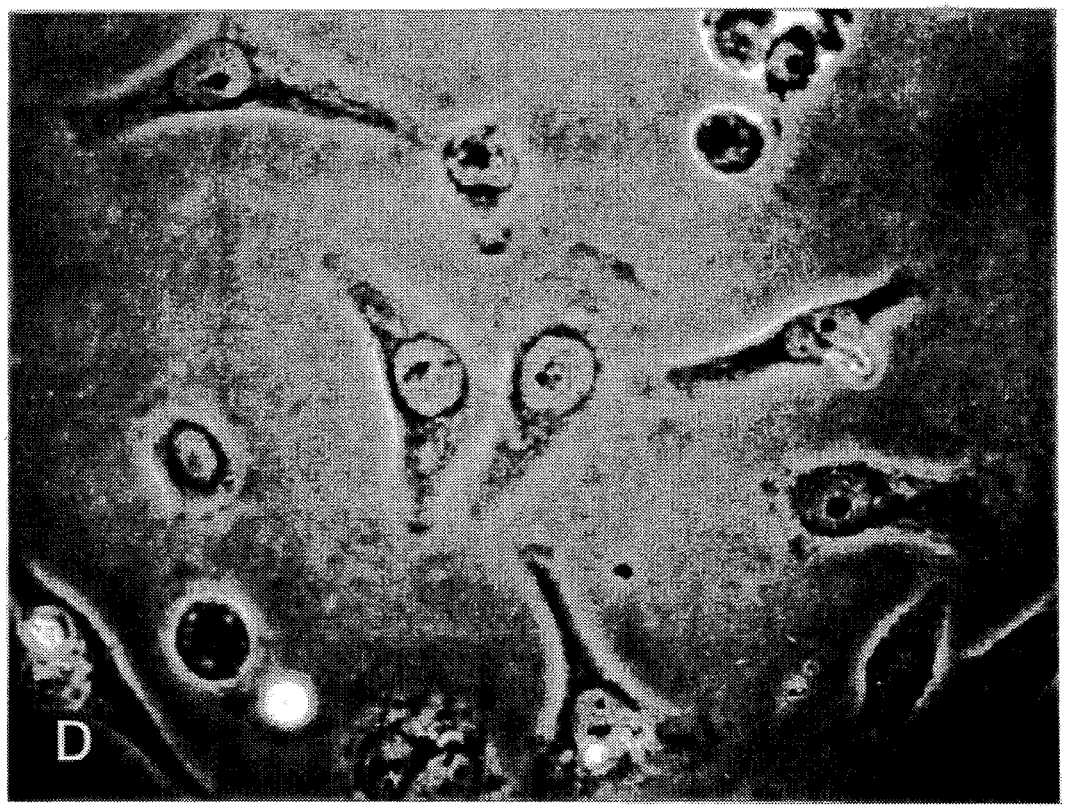

EXAMPLE 4: In vivo incubation of cells with probe and fixation of the treated cells after 16 hours incubation followed by freezing and later detection of probe targeting HEp-2 cells at a concentration of $1.25\times10^6$ were incubated with 20.5 µl of probe mixtures containing 100 mg of p53 gene probe or Chromosome 17 alpha satellite DNA probe under the same protocols described in Examples 1 and 2. After one hour the probe-treated cells were suspended in 60 ml petri plates in conditioned and fresh DMEM media (1:4) and replaced in a $CO_2$ Incubator. After 16 hours the plates were washed with 1X PBS (which was saved together with the media removed from the plates for collection of loosened cells) and 3 ml of ice cold 100% ethanol was placed in each plate. Ethanol was removed after 10 minutes and the plates were frozen at −20° C. Saved PBS and media were centrifuged, the resulting cell pellet further washed with 1X PBS, and the cells fixed by gentle vortexing with 100% ice cold methanol. 24 hours after freezing the plates with fixed cells were allowed to come to room temperature, then incubated for 30 minutes with two ml of 1 mg/ml BSA in 1X PBS, followed by incubation in the dark with 1 ml of 10 μg/ml FITC-avidin in blocking solution for 30 minutes. The methanol-treated cells in suspension were washed with 1X PBS at room temperature and incubated in the dark with 10 μg/ml FITC-avidin in blocking solution without prior incubation in BSA-PBS. Following incubation with FITC-avidin the cells on plates and in suspension were rapidly rinsed with 4X SSC washes (as in Example 2), and FITC reporter targeting observed with microscopes in fluorescence and phase after mounting with antifade and coverslips. Specific FITC fluorescence was observed in approximately 20% of cells incubated with FITC-avidin in petri plates. Slightly more than 20% of the cells incubated with FITC-avidin in suspension had specific signal. FIGS. 3, 4, and 5 show several fluorescent and phase image examples of p53 and Chromosome 17 alpha satellite DNA probe mixture treated HEp-2 cells incubated with probe mixtures and fixed 16 hours later while still attached to plates. Although probe mixtures were incubated with cells in vivo, and probe bound to DNA targets in vivo, the cells were fixed and stored frozen for later in vitro detection of probe binding by means of reporter fluorescence.

Although the transformation and diagnostic method of the invention has been described with respect to certain embodiments and specific examples, it will be appreciated that various modifications of and changes to the method are possible without departing from the invention, the scope of which is defined in the claims set forth below.

I claim:

1. An in vitro method for the transfection of living mammalian cells comprising the steps of:

growing living mammalian cells under physiological conditions suitable for the growth of said cells;

preparing at least one stable nucleoprotein complex with a single-strand DNA sequence of a length of between 200 and 700 bases, and with RecA protein molecules bound to said single-strand DNA sequence, wherein said sequence is substantially identical or complementary to a genomic sequence in said mammalian cells;

mixing said nucleoprotein complex with said living cells, to form an incubation mixture, and;

incubating said incubation mixture for a sufficient period of time to allow said DNA sequence to be transformed into the genome of said cells, said transfection occurring without the additional assistance of a viral vector, calcium phosphate, DEAE-dextran precipitation, lipofection, electroporation, microinjection, or any artificial means for permeating the cell membranes of said cells.

2. The method for the transfection of living mammalian cells according to claim 1, further comprising the step of:

adding to said nucleoprotein complex the components of magnesium acetate of a concentration from between 8 to 20 mM and ATPγS, and incubating said incubation mixture for at least 30 minutes.

3. The method for the transfection of living mammalian cells according to claim 2, further comprising the steps of:

incubating said incubation mixture at a constant temperature; and selecting as said mammalian cells, cells from carcinoma tissue.

4. The method for the transfection of living mammalian cells according to claim 3, further comprising the steps of:

adding to said nucleoprotein complex the following components, in the following approximate quantities, to make a 20.5 μl mixture: 6.59 mM magnesium acetate, 24.39 mM sodium acetate, 0.49 mM DTT, 0.24 mM ATPγS, and 8.39 μM RecA.

* * * * *